United States Patent
Ochiya et al.

(10) Patent No.: US 8,106,024 B2
(45) Date of Patent: Jan. 31, 2012

(54) METHOD OF TREATING CANCER WITH AN RPN2 GENE EXPRESSION INHIBITOR

(75) Inventors: Takahiro Ochiya, Tokyo (JP); Kikuya Kato, Osaka (JP); Kimi Honma, Tokyo (JP); Yasuji Ueda, Tokyo (JP)

(73) Assignees: Taisho Pharmaceutical Co., Ltd., Tokyo (JP); Dainippon Sumitomo Pharma Co., Ltd., Osaka (JP); Japan as represented by President of National Cancer Center, Tokyo (JP); Koken Co., Ltd., Tokyo (JP)

( * ) Notice: Subject to any disclaimer, the term of this patent is extended or adjusted under 35 U.S.C. 154(b) by 71 days.

(21) Appl. No.: 12/304,888

(22) PCT Filed: Jun. 15, 2007

(86) PCT No.: PCT/JP2007/000637
§ 371 (c)(1),
(2), (4) Date: May 15, 2009

(87) PCT Pub. No.: WO2007/144985
PCT Pub. Date: Dec. 21, 2007

(65) Prior Publication Data
US 2010/0087507 A1    Apr. 8, 2010

(30) Foreign Application Priority Data
Jun. 16, 2006  (JP) .................. 2006-167886

(51) Int. Cl.
| C12N 15/11 | (2006.01) |
| C07H 21/04 | (2006.01) |
| A61K 39/395 | (2006.01) |
| C12Q 1/68 | (2006.01) |
| G01N 33/574 | (2006.01) |

(52) U.S. Cl. .................. 514/44 A; 536/24.5; 424/138.1; 435/6.1; 435/7.23

(58) Field of Classification Search .................. None
See application file for complete search history.

(56) References Cited

U.S. PATENT DOCUMENTS
5,856,097 A * 1/1999 Pinkel et al. .................. 435/6
2009/0246794 A1 * 10/2009 Madura et al. .................. 435/7.1

FOREIGN PATENT DOCUMENTS
WO    2005/003352    1/2005
WO    2005/007846    1/2005

OTHER PUBLICATIONS

Iwao-Koizumi et al., Prediction of docetaxel response in human breast cancer by gene expression profiling, 2005, Journal of Clinical Oncology, vol. 23, pp. 422-431.*
Minakuchi et al., Atelocollagen-mediated synthetic small interfering RNA delivery for effective gene silencing in vitro and in vivo, 2004, Nucleic Acids Research, vol. 32, No. 13, e109, pp. 1-7.*
Ito et al., Rad51 siRNA delivered by HVS envelope vector enhances the anti-cancer effect of cisplatin, 2005, The Journal of Gene Medicine, vol. 7, pp. 1044-1052.*
So, A. et al., Molecular Cancer Therapeutics, (2005) vol. 4, No. 12, pp. 1837-1849.
Lima, R.T. et al., Cancer Gene Therapy, (2004) vol. 11, No. 5, p. 309-316.
Herman, J.F. et al., Oncogene, (2006) vol. 25, No. 21, p. 3049-6058.
Leng, Q. et al., Cancer Gene Therapy, (2005) vol. 12, No. 8, p. 682-690.
Takei, Y. et al. Cancer Research, (2004) vol. 64, No. 10, 9. 3365-3370.
Hufton, S.E. et al., FEBS Letters, (1999) vol. 463, No. 1-2, p. 77-82.
Heys, S.D. et al., Clinical Breast Cancer (2002) Suppl. 2, p. S69-74.
Jordan, M.A. et al., Current Medicinal Chemistry. Anti-cancer agents, (2002) vol. 2, p. 1-17.
Rao, S. et al., Journal of the National Cancer Institute, (1992) vol. 84, p. 785-788.
Schiff, P.B. et al., Proceeding of the National Academy of Sciences of the U.S.A., (1980) vol. 77, p. 1561-1565.
Stein, C.A., Seminars in oncology, (1999) vol. 26, p. 3-7.
Usami et al., "Selective Induction of the Tumor Marker Glutathione S-Transferase P1 by Proteasome Inhibitors" The Journal of Biological Chemistry, vol. 280, No. 26, pp. 25267-25276, 2005.
Extended European Search Report issued with respect to EP Application No. 07766944.8, dated Nov. 4, 2010.

* cited by examiner

*Primary Examiner* — Dana Shin
(74) *Attorney, Agent, or Firm* — Greenblum & Bernstein, P.L.C.

(57) ABSTRACT

The present invention uses an RPN2 gene expression inhibitor as a cancer cell growth inhibitor, which further includes a drug showing an anti-cancer action if desired, and is administered in combination with atelocollagen if desired. In addition, the present invention is an anti-cancer agent including such cancer cell growth inhibitor.

10 Claims, 9 Drawing Sheets

(a) RPN2 siRNA
→ : Apoptotic cells (b) Non-targeting siRNA

Suppression of RPN2 Expression by RNAi

Schedule of treatment for orthotopic breast tumors

Induction of apoptosis in MCF7-ADR tumor by siRNA-DOC treatment

METHOD OF TREATING CANCER WITH AN RPN2 GENE EXPRESSION INHIBITOR

TECHNICAL FIELD

The present invention relates to use of an RPN2 gene expression inhibitor, specifically a cancer cell growth inhibitor, an anti-cancer agent including the same cancer cell growth inhibitor, and a method of using an RPN2 gene expression inhibitor.

BACKGROUND ART

Taxanes (docetaxel, paclitaxel) are one kind of anti-cancer agents used in the treatment of breast cancer, lung cancer, stomach cancer and the like. For example, docetaxel is one of the most effective anti-cancer agents for the treatment of cancer, especially breast cancer (Non-patent Document 1, Non-patent Document 2). Docetaxel is used as a neoadjuvant since the administration of docetaxel before the surgical operation can lead to reduction of the tumor size and enhancing the success rate of the operation.

It has been reported that taxanes (taxane class of drugs) such as docetaxel function by inhibiting the kinetics of the microtubules, thereby stopping the cells at the M phase of the cell division, and subsequently activating the program of apoptosis (Non-patent Documents 2 to 5).

[Non-patent Document 1] Heys, S. D. et al., Clinical breast cancer, 2002, Suppl 2, p.S 69-74

[Non-patent Document 2] Jordan, M. A. et al., Current medicinal chemistry. Anti-cancer agents, 2002, Vol. 2, p. 1-17

[Non-patent Document3] Rao, S. et al., Journal of the National Cancer Institute, 1992, Vol. 84, p. 785-788 [Non-patent Document 4] Schiff, P. B. et al., Proceedings of the National Academy of Sciences of the United States of America, 1980, Vol. 77, p. 1561-1565

[Non-patent Document 5] Stein, C. A., Seminars in oncology, 1999, Vol. 26, p. 3-7

DISCLOSURE OF THE INVENTION

In the meantime, although taxanes are a very effective anti-cancer agent, it is known that about half of breast cancer patients do not respond to the chemical therapy by taxanes, only causing side-effect by the administration.

Accordingly, the present inventors have conducted gene expression profile analysis for some breast cancer-derived samples which showed response to the treatment (chemical treatment by taxanes is effective) (hereinafter, referred to as "responsive sample"), and other breast cancer-derived samples which showed no response to the treatment (chemical treatment by taxanes is ineffective) (hereinafter, referred to as "resistant sample"), and found that specific gene expression is high in common in the resistant samples. Based on this finding, the present inventors have conducted extensive studies on the relation between the specific gene expression and effectiveness of chemical treatment, and as a result thereof, reached the completion of the present invention.

Specifically, the present invention provides those of (1) to (13) as described below.

(1) A cancer cell growth inhibitor including an RPN2 gene expression inhibitor;

(2) A cancer cell growth inhibitor including an RPN2 gene expression inhibitor and a drug showing an anti-cancer action;

(3) The cancer cell growth inhibitor as described in (1) or (2); wherein the cancer cell growth inhibitor further includes atelocollagen;

(4) The cancer cell growth inhibitor as described in (1) or (2); wherein the RPN2 gene expression inhibitor is a low molecular compound;

(5) The cancer cell growth inhibitor as described in (4); wherein the RPN2 gene expression inhibitor is a low molecular compound which suppresses RPN2 gene expression by RNA interference;

(6) The cancer cell growth inhibitor as described in (5); wherein the low molecular compound is siRNA which has a sequence corresponding to a predetermined sequence of the RPN2 gene;

(7) The cancer cell growth inhibitor as described in (2); wherein the drug showing an anti-cancer action is at least one selected from taxanes;

(8) The cancer cell growth inhibitor as described in (2); wherein the drug showing an anti-cancer action is at least one selected from platinum-based chemotherapy drugs;

(9) The cancer cell growth inhibitor as described in any one of (1) to (8); wherein the cancer cell growth inhibitor promotes the apoptosis of cancer cells;

(10) An anti-cancer agent including the cancer cell growth inhibitor as described in any one of (1) to (9);

(11) A method of using an RPN2 gene expression inhibitor as an anti-cancer agent;

(12) A method of using an RPN2 gene expression inhibitor as an anti-cancer agent in combination with a drug showing an anti-cancer action;

(13) The method of using an RPN2 gene expression inhibitor as described in (11) or (12); wherein atelocollagen is further combined.

According to the present invention, there is provided novel use of an RPN2 gene expression inhibitor.

BRIEF DESCRIPTION OF THE DRAWINGS

The above and other objects, features and advantages of the present invention will be more apparent from the following description of certain preferred embodiments taken in conjunction with the accompanying drawings.

BEST MODE FOR CARRYING OUT THE INVENTION

Figure 1:
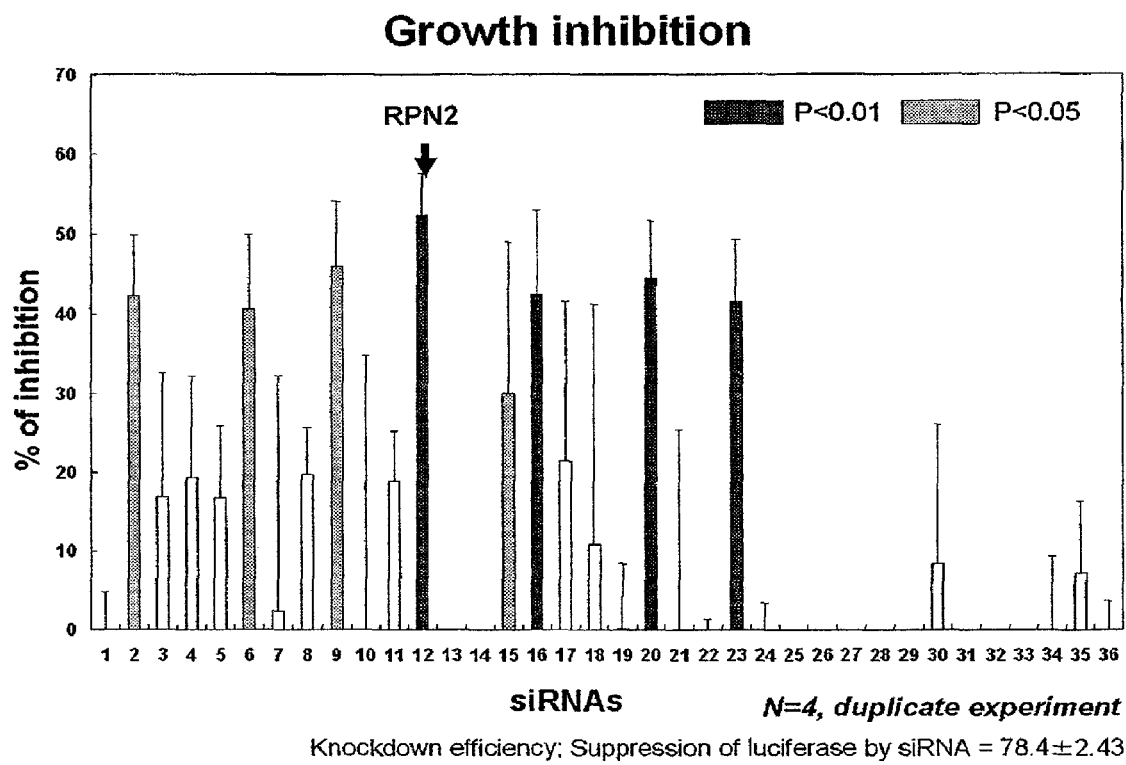
FIG. 1 is a graph showing the cell growth inhibition rate by introduction of siRNA which are targeted to each gene shown in Table 1 in a drug-resistant cell.

The present invention will be now described herein with embodiments.

It has been found by the present inventors that when cancer cells collected from a cancer patient are treated with a drug showing an anti-cancer action, for example, at least one selected from taxanes such as docetaxel, paclitaxel and the like, they are divided into two groups: cancer cells which show response to the drug, and cancer cells which show no response. In addition, gene expression change was investigated for the cancer cells which show no response to the drug. As a result, there was found the expression level increase of various genes including RPN2 gene.

Accordingly, screening has been performed for the drug response of cancer cells by conducting a silencing experiment of the gene which has shown increase of expression level. As a result, it has been found that when RPN2 gene expression is suppressed in the cancer cells showing no drug response, the drug response is observed in these cancer cells, that is, apoptosis is promoted by a drug showing an anti-cancer action to the cancer cells.

On the other hand, it has been also found that apoptosis of these cancer cells is promoted only with suppression of RPN2 gene expression, even without combination with a drug showing an anti-cancer action to cancer cells.

Accordingly, in one aspect, the present invention provides a cancer cell growth inhibitor including an RPN2 gene expression inhibitor, or including an RPN2 gene expression inhibitor and a drug showing an anti-cancer action as described above.

Herein, the drug showing an anti-cancer action includes not only a drug such as taxanes acting on the microtubule, but also a metabolic antagonist, a DNA-alkylating agent, a DNA binder (platinum-based chemotherapy drugs), anti-carcinogenic antibiotics and the like. Specifically, it includes amrubicin hydrochloride, irinotecan hydrochloride, ifosfamide, etoposide, gefinitib, cyclophosphamide, cisplatin, trastuzumab, 5-fluorouracil, mitomycin C, imatinib mesylate, methotrexate, rituximab, adriamycin and the like. In addition, such a drug which shows anti-cancer action may be used alone, or in combination of two or more kinds.

Moreover, applicable cancer cell includes various cancer cells such as breast cancer cell, stomach cancer cell, colon cancer cell, lung cancer cell, prostate cancer cell and blood-cell cancer cell.

Herein, RPN2 (ribophorin II) exists in the intracellular follicle, and is one of molecules (subunit) constituting a oligosaccharyl transferase complex which is involved in glycosylation of a protein. For activation of this enzyme, a subunit including STT3 is known as essential, but RPN2 is not clearly known for its function. In addition, RPN2 gene is a gene encoding this RPN2 subunit, which has a base sequence shown in Sequence No. 1.

Moreover, the RPN2 gene expression inhibitor is a drug which suppresses RPN2 gene expression, and a low molecular compound, for example, a low molecular compound which suppresses RPN2 gene expression by RNA interference.

Herein, RNA interference is a phenomenon of suppressing gene expression specifically to the sequence by low molecular non-coding double chain (ds) RNA molecule. For example, it refers to target mRNA cleavage by si (small interfering) RNA, gene silencing of target DNA region by siRNA through heterochromatin formation, translation suppression by mi (micro) RNA, transcription suppression, mRNA breakdown and the like.

siRNA is preferably used in the embodiments of the present invention from the view that it can be designed for its sequence based on the sequence of the subject gene, i.e., RPN2 gene, and can be prepared artificially.

Specifically, the low molecular compound used as the RPN2 gene expression inhibitor is preferably siRNA which has a sequence corresponding to the predetermined sequence of RPN2 gene, specifically a sequence corresponding to a part of the targeted mRNA. One specific example of such sequence includes dsRNA including RNA of Sequence No. 3 which becomes the sense chain, and RNA of Sequence No. 4 which becomes the antisense chain for the sequence of $1194^{th}$ to $1212^{th}$ (Sequence No. 2) in the RPN2 gene sequence shown in Sequence No. 1. The double chain moiety becomes 19 base lengths since the 3' end of each chain in this dsRNA has an overhang of 2 bases.

Such siRNA is synthesized chemically. For example, it is obtained by successive condensation reaction per one base from 3' end toward 5' end by phosphoamidide method which is also used in DNA chemical synthesis. However, this reaction is carried out with the protection of the 2' end hydroxide group of respective ribonucleotide in order to prevent cleavage by RNase in the synthesis process. This protection group includes 2'-O-t-butyldimethylsilyl (2'-tBDMS) group, 2'-O-triisopropylsilyloxymethyl (2'-TOM) group, 5'-silyl-2'-acetoxyethoxy (2'-ACE) group and the like.

Herein, target mRNA cleavage by siRNA is considered to proceed with the reaction mechanism as described below.

siRNA double-stranded chain is incorporated into the intracellular protein complex RISC (RNA-induced Silencing Complex) and bound to it, and the sense chain is eliminated. Subsequently, the target mRNA is incorporated into RISC, and the antisense chain bound to RISC, recognizes the complimentary sequence of the mRNA and is bound to it. Furthermore, the mRNA bound to the antisense chain is specifically cleaved.

For example, as a method of suppressing the gene expression by acting on mRNA, an antisense method is known including binding to an antisense chain which is complimentary to the mRNA, thereby inhibiting the translation into a protein. However, this method has a problem that the artificial antisense nucleic acid has a weak activity since it may not be effectively bound to the target site by the influence of the mRNA conformation.

On the other hand, as for the RNA interference using siRNA, the problem of weak activity depending on the local structure of mRNA is reduced due to the action regardless of the mRNA conformation.

Moreover, miRNA is known to be a low molecular RNA not encoding a protein, and exists on the genome in hundreds of kinds. miRNA is transcribed as a nucleotide of hundreds to thousands of bases, then subjected to a processing to be a final dimer nucleotide of 19 to 24 bases. This miRNA suppresses gene expression by mRNA translation control, mRNA cleavage, mRNA transcription control and the like wherein the mRNA has a base sequence complimentary to this miRNA.

Since RPN2 is also known to be controlled in expression by multiple miRNAs, it is possible to artificially synthesize such miRNA, and use it to suppress RPN2 gene expression. A known miRNA sequence which is likely to suppress RPN2 gene expression can be searched through a published database (Target Scan Release 3.1 and the like).

Moreover, in another aspect, the present invention provides a drug delivery system of a cancer cell growth inhibitor. Specifically, the cancer cell growth inhibitor further includes atelocollagen.

Herein, atelocollagen is an enzyme-soluble collagen and a modification thereof. The modification includes chemical modification of side chain amino group or carboxyl group, or chemical/physical cross-linking. In addition, any collagen can be also used derived from a mammalian animal such as cow, pig, horse and human, a bird or a fish. However, the collagen is desired to be not changeable with the temperature of the environment to be used, i.e., to have thermal stability. Specifically, there can be used a collagen derived from a mammalian animal or a bird, or a collagen obtained by production from the culture cells or gene recombination thereof. The type of the collagen is not especially limited, but types I, II and III or the like can be used in view of availability.

The combination with such atelocollagen makes it possible to effectively deliver the cancer cell growth inhibitor to the target cells, and effectively incorporate it into the cells.

In still another aspect, the present invention provides use of the RPN2 gene expression inhibitor as described above.

For example, an RPN2 gene expression inhibitor can be administered to a cancer patient, with the atelocollagen if desired, and used as an anti-cancer agent to promote apoptosis of the cancer cells. Alternatively, an RPN2 gene expression inhibitor can be administered to a cancer patient together with a drug showing an anti-cancer action, and with the atelocollagen if desired, and used as an anti-cancer agent to promote apoptosis of the cancer cells. In addition, the actions of the RPN2 gene expression inhibitor onto the cells are not limited to promoting apoptosis, but may induce ultimate cell death and suppress cell growth, and it is useful as a cancer cell growth inhibitor.

Specifically, the present invention provides a method of using an RPN2 gene expression inhibitor as an anti-cancer agent, and a method of using an RPN2 gene expression inhibitor in combination with a drug showing an anti-cancer action as an anti-cancer agent. In addition, in another aspect, the present invention provides an anti-cancer agent including the cancer cell growth inhibitor as described above.

For such applications, the dosages of the RPN2 gene expression inhibitor, the drug and the atelocollagen vary depending on administration method, and kind and size of the tumor. However, for example, for the RPN2 gene expression inhibitor, the amount is desirably equal to or more than 1 nmol/kg and equal to or less than 10 nmol/kg in the local administration, and equal to or more than 2 nmol/kg and equal to or less than 50 nmol/kg in the systemic administration. In addition, in case that the drug is used, the drug amount to be used is desirably determined based on the amount to be used when each drug is used alone. In case that the drug is combined with atelocollagen, the concentration of this atelocollagen is desirably, for example, equal to or more than 1 mg/ml (w/vol) and equal to or less than 50 mg/ml (w/vol) in the local administration, and equal to or more than 0.1 mg/ml (w/vol) and equal to or less than 30 mg/ml (w/vol) in the systemic administration. However, after the mixing with the RPN2 gene expression inhibitor, the amount to be used is desirably equal to or more than 5 ml and equal to or less than 100 ml in the local administration, and equal to or more than 10 ml and equal to or less than 500 ml in the systemic administration.

According to such use, an RPN2 gene expression inhibitor, in combination with a drug showing an anti-cancer action if desired, induces cell death or suppresses cell growth with the mechanism of promoting apoptosis of the cancer cells or the like, and as a result, makes it possible to perform cancer treatment.

EXAMPLES

The present invention will now be explained based on Test Examples, but the present invention is not limited to the Test Examples.

Test Example 1

Cell Growth Suppression Test (1) Preparation of Atelocollagen Cell Transfection Array ATAC-PCR analysis (International Patent Application No. 2005/003352 pamphlet) was carried out in the cancer tissue of a patient showing no drug response when treated with docetaxel as a drug showing an anti-cancer action. As a result, siRNA was synthesized for the 36 genes below which showed expression increase.

TABLE 1

| No. | rank * | accession_number | symbol | description |
|---|---|---|---|---|
| 1 | 2 | BC005193 | HP12198 | hypothetical protein 12198 |
| 2 | 4 | AF052159 | 24416 | *Homo sapiens* clone 24416 mRNA sequence. |
| 3 | 5 | M38591 | S100A10 | S100 calcium-binding protein A10 (annexin II ligand, calpactin I, light polypeptide (p11)) |
| 4 | 6 | Y00486 | APRT | adenine phosphoribosyltransferase |
| 5 | 7 | X95404 | CFL1 | cofilin 1 (non-muscle) |
| 6 | 8 | M24485 | GSTP1 | *Homo sapiens* glutathione S-transferase pi (GSTP1) gene |
| 7 | 9 | M19645 | GRP78 | Human 78 kdalton glucose-regulated protein (GRP78) gene |
| 8 | 10 | BC000672 | GNB2L1 | guanine nucleotide binding protein (G protein), beta polypeptide 2-like 1 |
| 9 | 11 | BC001002 | TUBB1 | tubulin beta |
| 10 | 12 | M33882 | MX1 | *Homo sapiens* interferon-induced protein p78 (MX1) gene |
| 11 | 13 | BC001005 | COX7C | cytochromec oxidase subunit VIIc |
| 12 | 15 | Y00282 | RPN2 | ribophorin II |
| 13 | 16 | U32944 | HDLC1 | dynein, cytoplasmic, light polypeptide |
| 14 | 18 | U25165 | FXR1 | fragile X mental retardation, autosomal homolog 1 |
| 15 | 19 | AF151802 | CGI-44 | CGI-44 protein, sulfide dehydrogenase like (yeast) |
| 16 | 20 | AL135819 | NDUFS3 | *Homo sapiens*, NADH dehydrogenase (ubiquinone) Fe—S protein 3 |
| 17 | 21 | AL358933 | EST | ESTs |

TABLE 1-continued

| No. | rank * | accession_number | symbol | description |
|---|---|---|---|---|
| 18 | 22 | BC003639 | R33729 1 | *Homo sapiens*, Similar to hypothetical protein R33729 1 |
| 19 | 25 | AF052955 | ATP5E | ATP synthase, H+ transporting, mitochondrial F1 complex, epsilon subunit |
| 20 | 27 | AF014955 | TFAR19 | programmed cell death 5 |
| 21 | 30 | AL137440 | CRR9p | cisplatin resistance related protein CRR9p |
| 22 | 31 | X91195 | SOM172 | phospholipase C, beta 3, neighbor |
| 23 | 32 | AK026857 | LOC63875 | ribosomal protein L17 isolog |
| 24 | 33 | BC006481 | TUBA1 | tubulin, alpha, ubiquitous |
| 25 | 34 | X02492 | IFI-6-16 | interferon, alpha-inducible protein (clone IFI-6-16) |
| 26 | 36 | BC004319 | GAPDH | glyceraldehyde-3-phosphate dehydrogenase |
| 27 | 37 | BC006455 | SLC25A3 | solute carrier family 25 (mitochondrial carrier: phosphate carrier), member 3 |
| 28 | 38 | AF157482 | MAD2L2 | MAD2 (mitotic arrest deficient, yeast, homolog)-like 2 |
| 29 | 39 | X89593 | CTNNB1 | catenin (cadherin-associated protein), beta 1 (88 kD) |
| 30 | 41 | M84739 | CALR | calreticulin |
| 31 | 42 | BC000547 | MRPS6 | *Homo sapiens*, clone IMAGE: 2958115, mRNA, partial cds |
| 32 | 44 | AF007150 | FLJ90245 | *Homo sapiens* clone 23767 and 23782 mRNA sequences |
| 33 | 46 | Z26876 | RL38 | ribosomal protein L38 |
| 34 | 47 | AY007104 | EST | EST |
| 35 | 48 | BC004325 | ENO1 | enolase 1, (alpha) |
| 36 | 50 | M20456 | ALDH2 | aldehyde dehydrogenase 2 family (mitochondrial) |

Subsequently, based on the method described in Japanese Patent Application Laid-Open (JP-A) No. 2006-6262, the mixture of atelocollagen (manufactured by KOKEN CO., LTD.) and siRNA corresponding to each gene, was coated onto a 96 well microplate, to prepare an atelocollagen cell transfection array which can do reverse transfection of siRNA.

(2) Cell Establishment

Luciferase gene (GL3) was stably transfected into multi-drug-resistant MCF7-ADR cells of which the parental Cell line is MCF7 breast cancer cell. The cell line was expressing luciferase and designated as MCF7-ADR-Luc.

(3) Measurement of Cell Growth Inhibition Rate and siRNA Introduction Efficiency The MCF7-ADR-LUC cell obtained in (2) was inoculated into the array prepared in (1) in 4×10³ cell number/well, and cultured for 3 days in the presence of 1 nM docetaxel (DOC). To the live cells were added luciferin, and from the luminescence value, cell growth inhibition rate and luciferase siRNA introduction efficiency were measured.

The cell growth inhibition rate was calculated with the control siRNA (dsRNA including a sense chain of Sequence No. 5 and an antisense chain of Sequence No. 6) as 100%. The results are shown in FIG. 1. In addition, the horizontal axis in FIG. 1 corresponds to the gene No. shown in Table 1. According to FIG. 1, introduction of siRNA corresponding to each gene suppressed cell growth in several genes in addition to RPN2 gene (No. 12).

Moreover, siRNA introduction efficiency was evaluated with the suppression rate of the luciferase activity by introduction of luciferase siRNA (GL3siRNA: dsRNA including a sense chain of Sequence No. 7 and an antisense chain of Sequence No. 8), separately from siRNA corresponding to each gene. In addition, luciferin (0.5 mM final concentration: Promega KK) was added to the medium, and the luciferase activity was measured immediately by a luminescence plate reader (ARVO: PerkinElmer, Inc.). Introduction of GL3 siRNA suppressed the luciferase activity by 80% in comparison with the control siRNA.

Test Example 2

Apoptosis Induction Test

A reagent for measurement of apoptosis was added to the plate after the measurement of the luciferase activity in Test Example 1, and the Caspase activity was measured. Specifically, the assay was conducted according to the protocol suggested by Promega KK (Apo-ONE Homogeneous Caspase-3/7 Assay), and the Caspase activity was measured 90 minutes after the addition of the reagent by a fluorescence plate reader (ARVO: PerkinElmer, Inc.). The Caspase activation rate was calculated with the control siRNA as 0%.

Moreover, in addition to the Caspase activity, apoptosis induction was investigated with observation by Hoechst staining (the cells were washed with PBS (−), added with 4% PFA-0.1% Triton X-100-1 mg/ml Hoechst 33342/in PBS (−), and fixed and stained at room temperature for 20 minutes. The cells were washed with PBS (−), and then observed under fluorescence microscope.).

Figure 2:
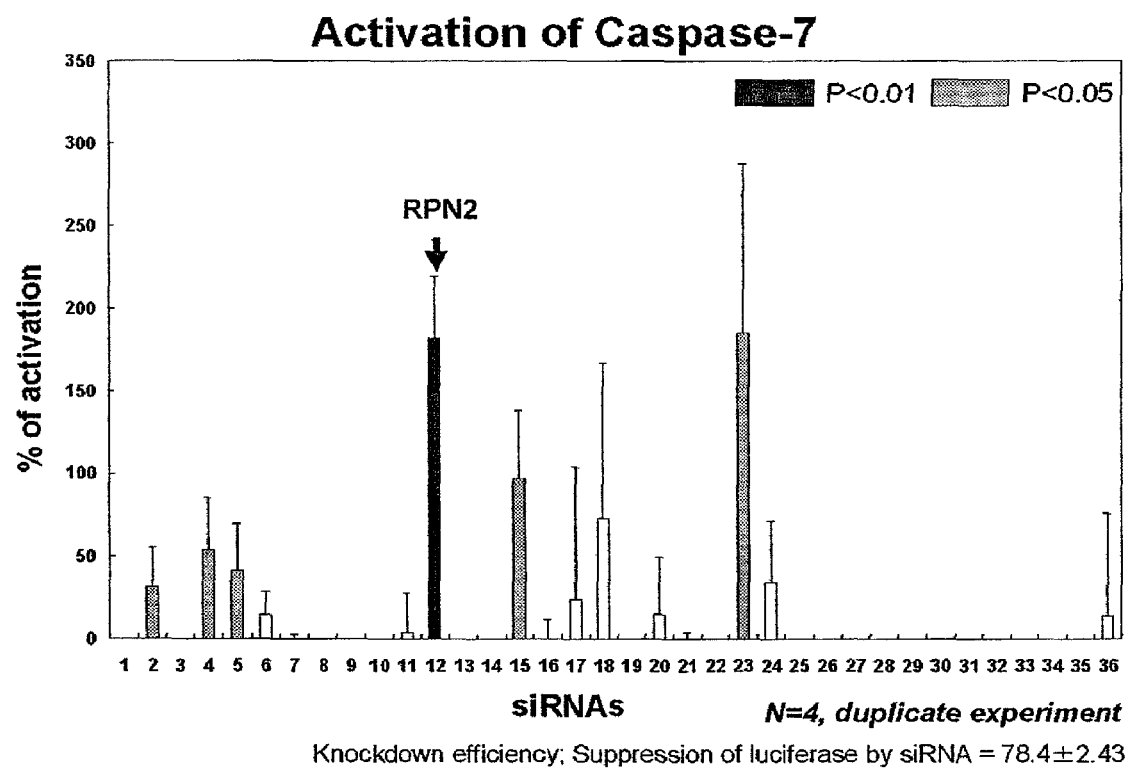
FIG. 2 is a graph showing the apoptosis induction rate by introduction of siRNA which are targeted to each gene shown in Table 1 in a drug-resistant cell.
Figure 3:
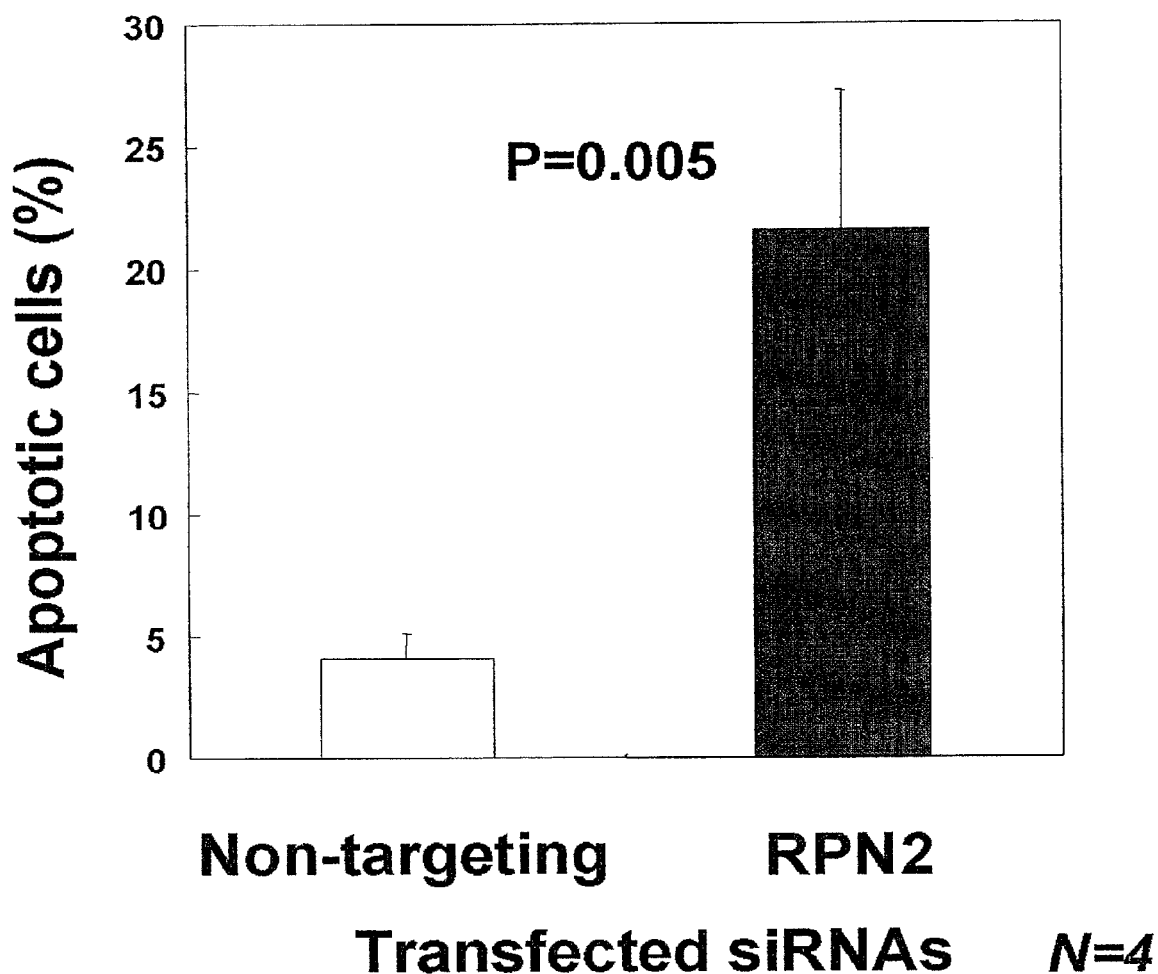
FIG. 3 is a graph showing the ratio of apoptosis cells which has been induced by siRNA.

The results are shown in FIG. 2. According to FIG. 2, introduction of siRNA for RPN2 gene (RPN2 siRNA) induced strongly Caspase activity. In addition, the ratios of the apoptosis cells (Apoptotic cells (%)) were compared by Hoechst staining between in the cells where RPN2 siRNA was introduced and in the cells where the control siRNA was introduced. As shown in FIG. 3, significant difference was seen. Specifically, it was suggested that apoptosis was induced by introduction of RPN2 siRNA.

Figure 4:
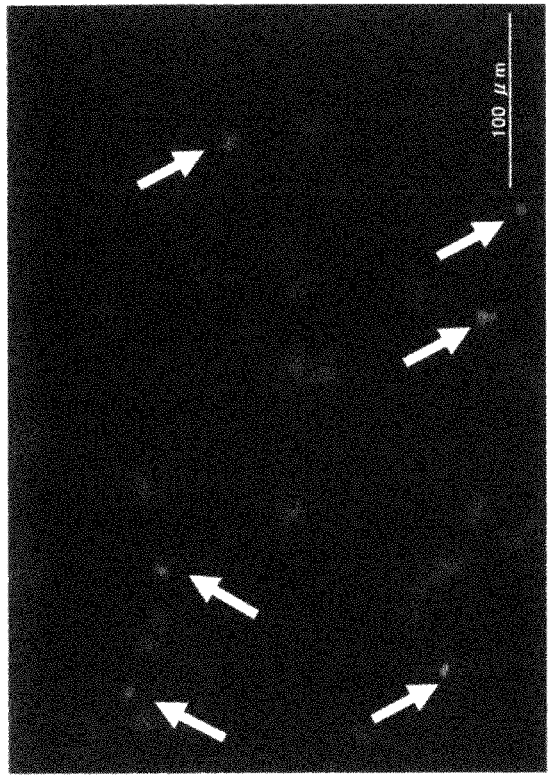
FIG. 4(a) and FIG. 4(b) are a view of the apoptosis cells observed by cell nucleus Hoechst staining.
Figure 4:
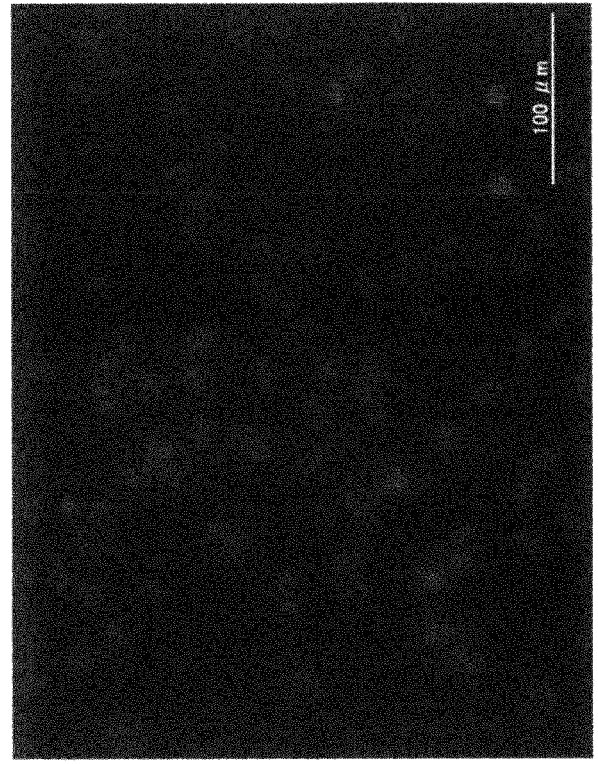

FIG. 4 shows the results of the observation for nucleus morphology by Hoechst staining. FIG. 4(*a*) shows the results of the system to which RPN2 siRNA was introduced, and FIG. 4(*b*) shows the results of the system to which control siRNA not suppressing any gene expression was introduced. According to FIG. 4, from the change of the nucleus morphology (aggregation, fragmentation), it was suggested that when RPN2 siRNA is introduced, apoptosis is induced.

Test Example 3

RPN2 Gene Expression Suppression Test

Into the atelocollagen cell transfection array prepared in Test Example 1 (1) were inoculated MCF7-ADR-Luc cells. After 3 days, cDNA was synthesized directly from the cell lysate, and real-time PCR was conducted, to investigate the RPN2 gene expression amount (SuperScript III Platinum CellsDirect Two-Step qRT-PCR: Invitrogen).

Figure 5:
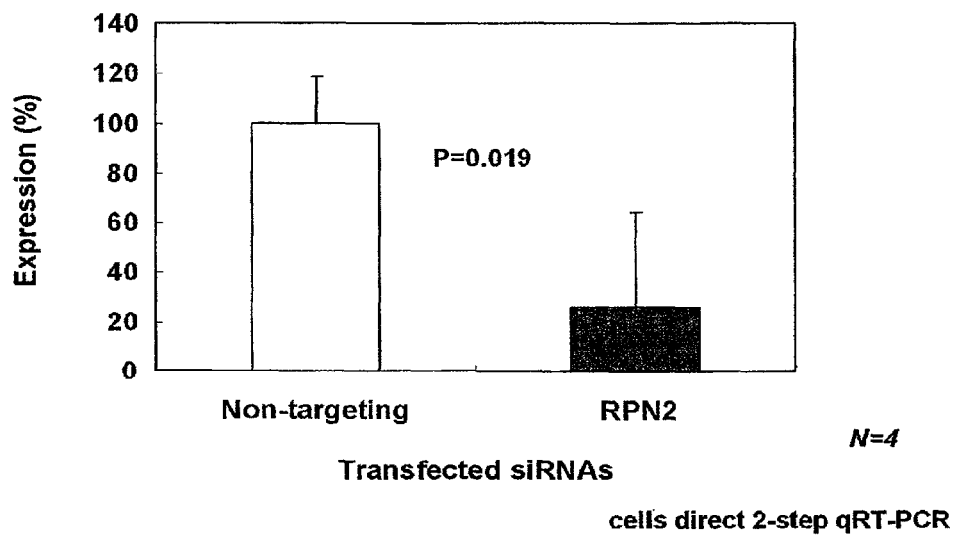
FIG. 5 is a graph showing the expression amount of RPN2 gene suppressed by siRNA.

The results are shown in FIG. 5. According to FIG. 5, it was found that introduction of RPN2 siRNA (dsRNA including a sense chain of Sequence No. 3 and an antisense chain of Sequence No. 4) suppressed RPN2 gene expression to about 25%.

Test Example 4

Tumor Growth Test in a Nude Mouse

Figure 6:
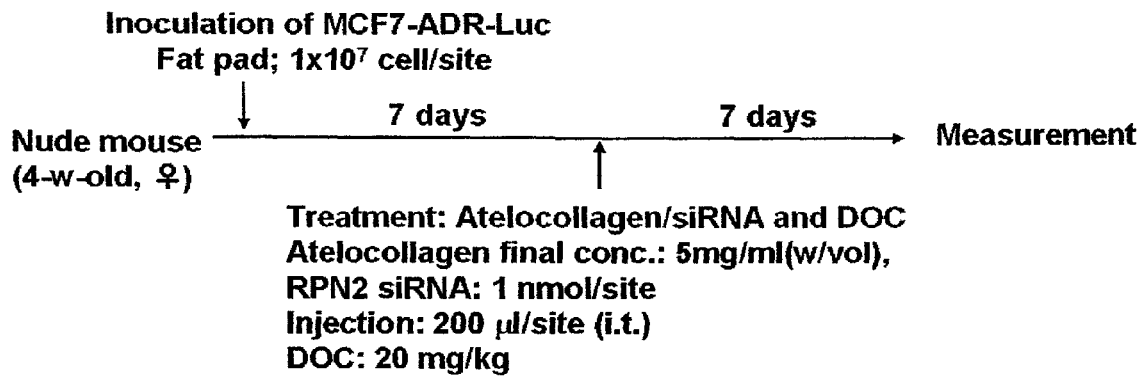
FIG. 6 is a view showing a protocol of the tumor growth test in a nude mouse.

According to the protocol shown in FIG. 6, $1 \times 10^7$ MCF7-ADR-Luc cells suspended in 100 μl PBS (−) were transplanted into the mammary fat pad of the nude mouse (4 weeks old, scalpel). After 7 days when the tumor radius reached about 5 mm, siRNA and DOC were administered. Herein, atelocollagen in the final concentration of 5 mg/ml (w/vol) and siRNA in 1 nmol per tumor were mixed, and then 200 μl of atelocollagen (manufactured by KOKEN CO., LTD.)/siRNA was administered into the tumor. At the same time, 20 mg/kg of docetaxel was administered into the abdominal cavity. After 7 days, the tumor radius was measured to compare the tumor volumes.

Figure 7:
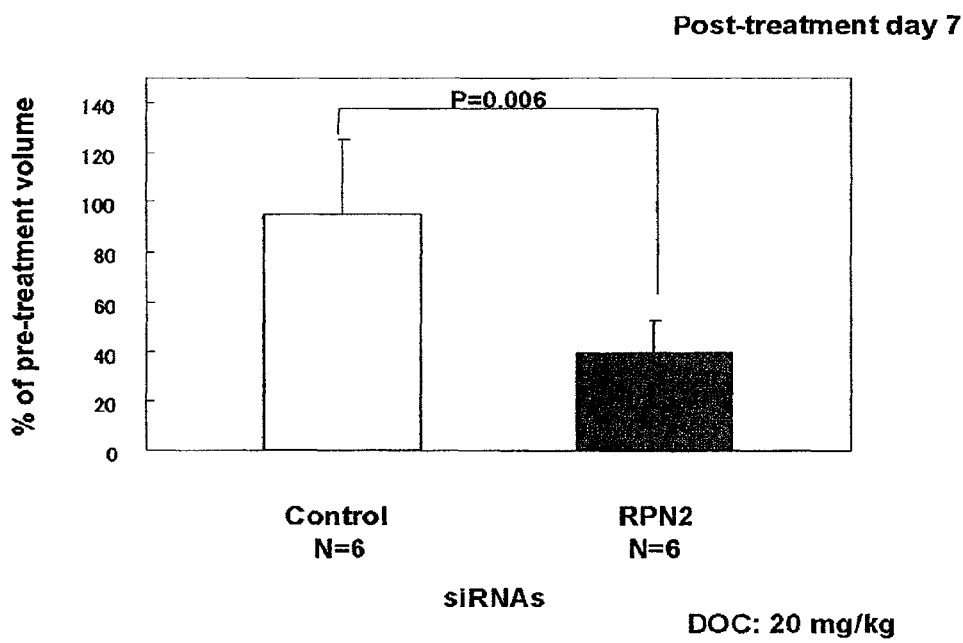
FIG. 7 is a graph showing the test results conducted in FIG. 6.

Results are shown in FIG. 7. According to FIG. 7, as a result of administration of RPN2 siRNA and DOC, significant tumor shrinkage was found in comparison with the control siRNA. It is considered that response to DOC was obtained by administration of RPN2 siRNA even in the cells showing no response to DOC.

Test Example 5

RPN2 Gene Expression Suppression Test in a Nude Mouse $1 \times 10^7$ MCF7-ADR-Luc cells suspended in 100 μl PBS (−) were transplanted into the mammary fat pad of the nude mouse (4 weeks old, scalpel). After 7 days, RPN2 siRNA and DOC were administered. Herein, atelocollagen in the final concentration of 5 mg/ml (w/vol) and RPN2 siRNA in 1 nmol per tumor were mixed, and then 200 μl of atelocollagen/siRNA was administered into the tumor. At the same time, 20 mg/kg of docetaxel was administered into the abdominal cavity. After 1 day, the tumor was collected and the total RNA was isolated, and RPN2 gene expression amount was measured with real-time RT-PCR (SYBR ExScript RT-PCR Kit: TaKaRa, LightCycler Real-Time PCR System: F. Hoffmann-La Roche Ltd.).

Figure 8:
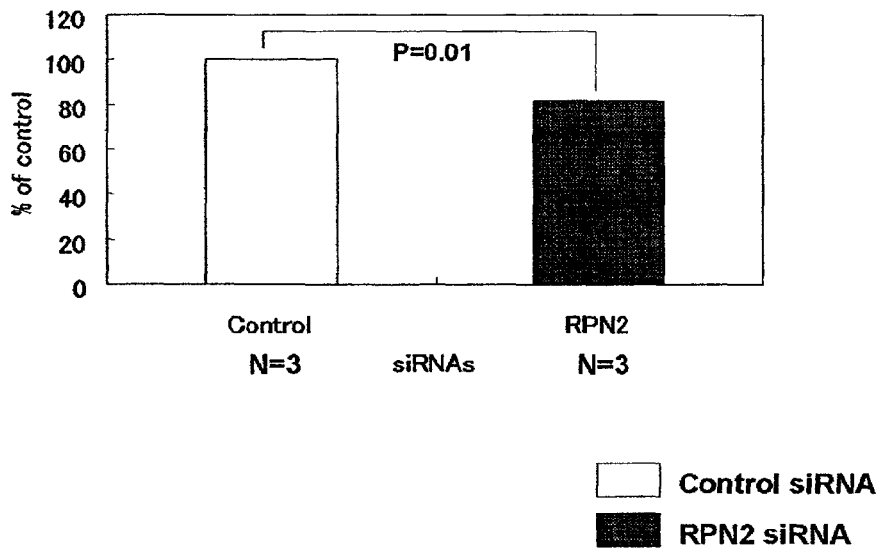
FIG. 8 is a graph showing the results of the RPN2 gene expression suppression test in a nude mouse.

The results are shown in FIG. 8. According to FIG. 8, RPN2 gene expression was suppressed by about 20% in the RPN2 siRNA administration group in comparison with the control siRNA administration group. In addition, the standard deviation is very small, thus not shown in the graph.

Test Example 6

RPN2 Gene Expression Suppression Test in a Nude Mouse

The RPN2 gene expression amount was measured in the same method as Test Example 5 except that RPN2 siRNA and DOC were administered at 6 weeks after MCF7-ADR-Luc cells were transplanted into the mammary fat pad of the nude mouse (4 weeks old, scalpel).

Figure 9:
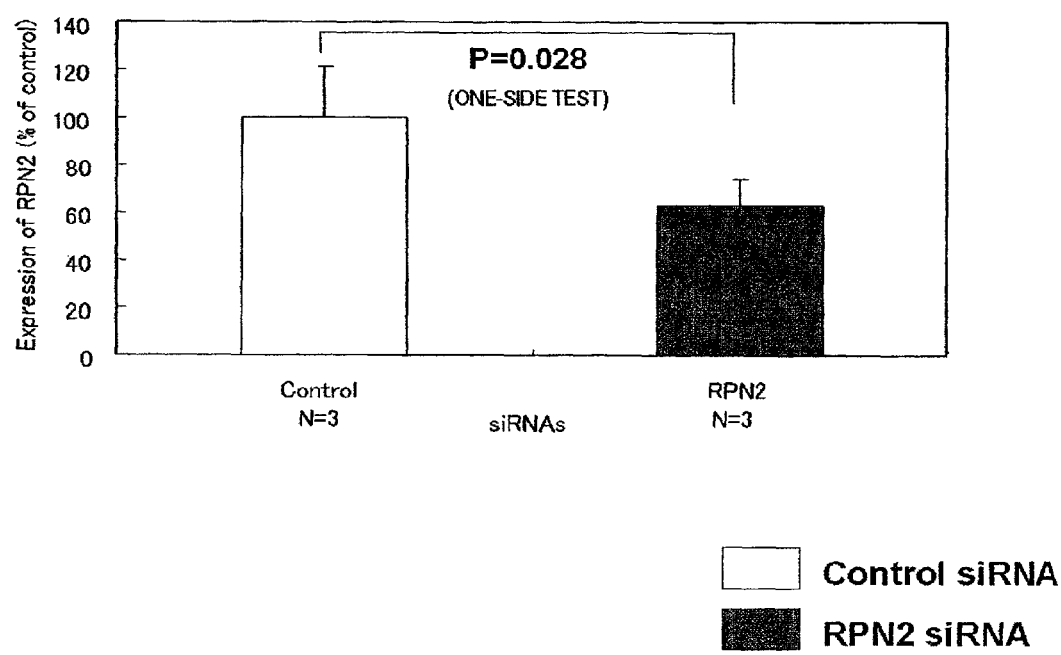
FIG. 9 is a graph showing the results of the RPN2 gene expression suppression test in a nude mouse.

The results are shown in FIG. 9. According to FIG. 9, RPN2 gene expression was suppressed by about 40% in the RPN2 siRNA administration group in comparison with the control siRNA administration group.

Test Example 7

Apoptosis Induction Test in a Nude Mouse $1 \times 10^7$ MCF7-ADR-Luc cells suspended in 100 μl PBS (−) were transplanted into the mammary fat pad of the nude mouse (4 weeks old, scalpel). After 6 weeks, siRNA and DOC, or siRNA alone was administered. Atelocollagen in the final concentration of 5 mg/ml (w/vol) and siRNA in 1 nmol per tumor were mixed, and then 200 μl of atelocollagen/siRNA was administered into the tumor. At the same time, 20 mg/kg of docetaxel was administered into the abdominal cavity. After 4 days, the tumor was collected, and subjected to TUNEL staining (In Situ Cell Death Detection Kit: F. Hoffmann-La Roche Ltd.). The nucleus was subjected to counter staining with DAPI (4',6-diamidino-2-phenylindole).

Figure 10:
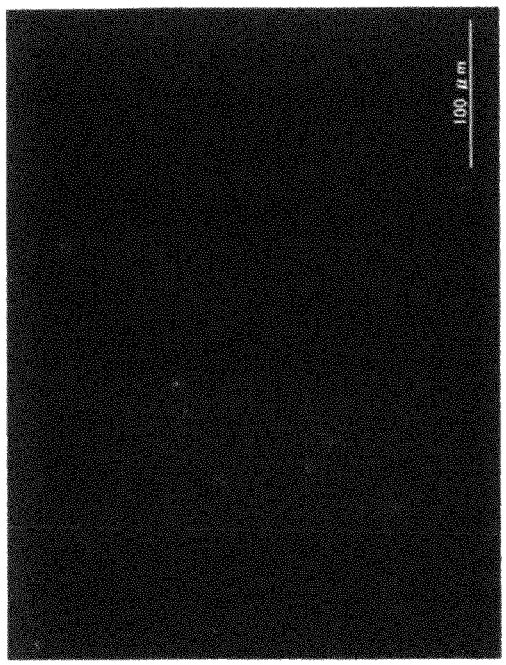
FIG. 10 is a view showing the results of the apoptosis induction test in a nude mouse.
Figure 10:
Figure 10:
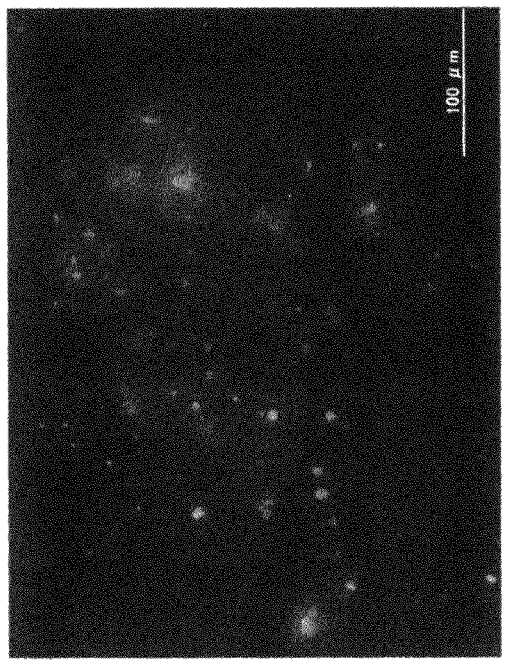
Figure 10:
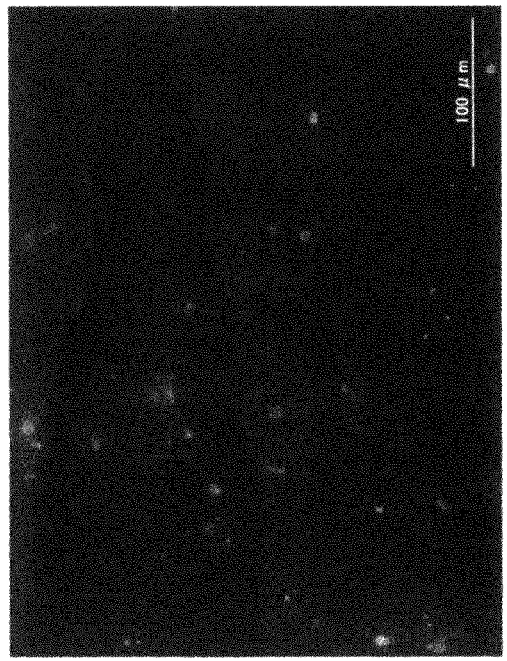

The results are shown in FIG. 10. According to FIG. 10, many apoptosis cells were found in the group to which both of DOC and RPN2 siRNA were administered.

Test Example 8

Into the atelocollagen cell transfection array prepared in Test Example 1 (1) were inoculated MCF7-ADR-Luc cells in the presence of or in the absence of a drug which shows anti-cancer action. After 3 days, Caspase activity was measured in the same way as described in Test Example 2.

Figure 11:
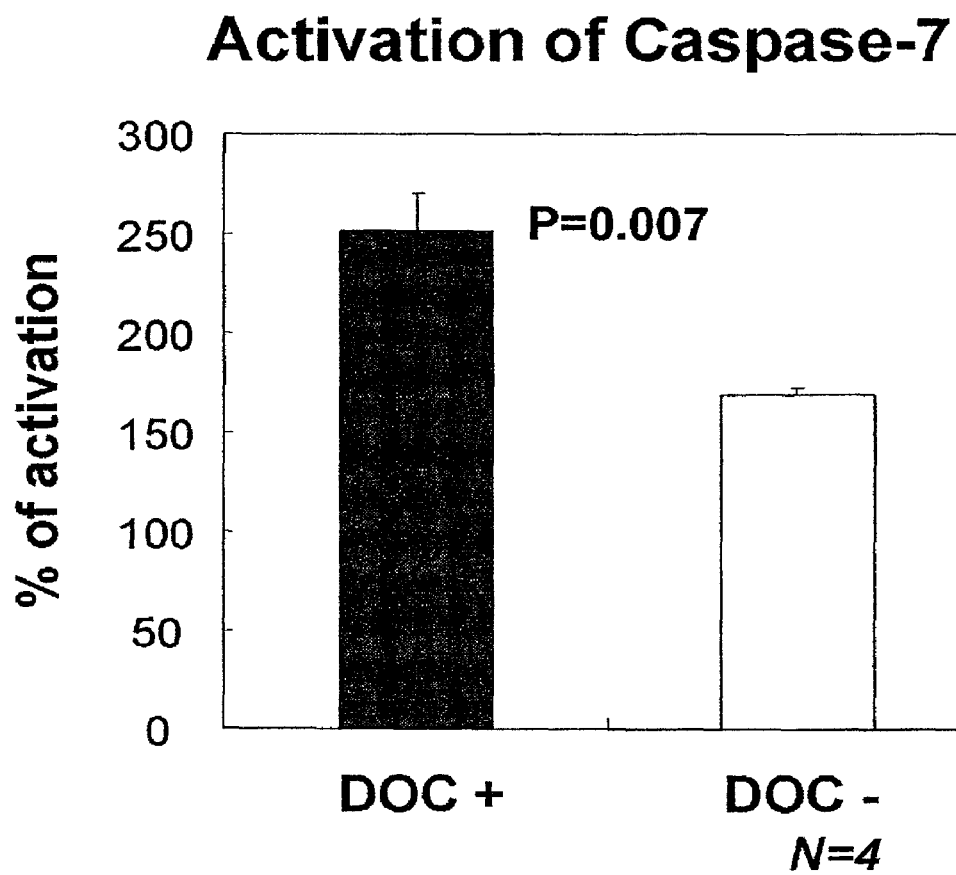
FIG. 11 is a graph showing the result of the RPN2 gene expression suppression test in the absence of the drug.

The results are shown in FIG. 11. According to FIG. 11, it was suggested that apoptosis is induced in the RPN2 siRNA-transduced cells even in the absence of DOC.

Test Example 9

To suppress RPN2 gene expression RPN2 siRNA was transduced into PC-9/CDDP cell which is a cell line of human lung cancer (small cell cancer, differentiated gland cancer), and resistant to cisplatin (Cis) that is a anti-cancer drug. Then, the cell was cultured for 3 days in the presence of or in the absence of cisplatin (0.3 μM). Then, Caspase activity was measured in the same way as described in Test Example 2. In addition, for comparison, the same test was conducted also for the system to which control siRNA not suppressing any gene expression was introduced.

Figure 12:
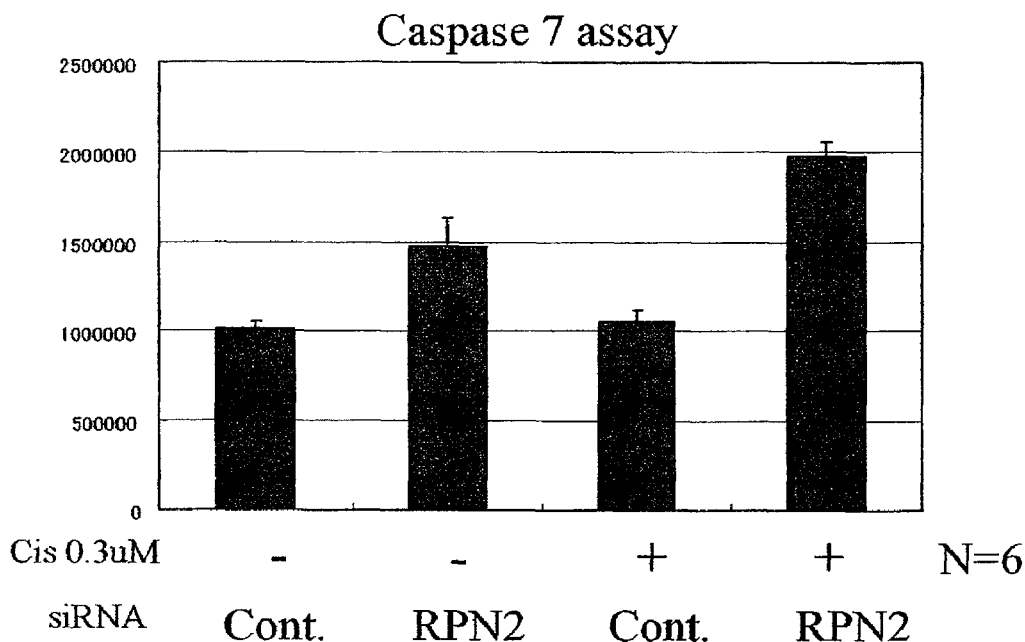
FIG. 12 is a graph showing the result of the RPN2 gene expression suppression test in cancer cells which shows no response to other kinds of drugs.

The results are shown in FIG. 12. According to FIG. 12, for control system, Caspase activity showed no difference both in the cisplatin (Cis)-untreated cells (Cis−) and the cisplatin-treated cells (Cis+). However, for the system into which RPN2 siRNA was introduced, it was suggested that apoptosis is induced regardless in the presence or absence of cisplatin. For the system into which RPN2 siRNA was introduced, significant apoptosis was induced, and cell death was found in the cisplatin-treated cells. Apoptosis increase was also found in the cisplatin-untreated cells, but it was slight as compared to the cisplatin-treated cells. In addition, though an example has been shown wherein cisplatin is used as a platinum-based chemotherapy drugs, it is considered that the same tendency will be seen for other platinum-based chemotherapy drugs which have less toxicity than that of cisplatin, for example, carboplatin and the like.

In addition, each Test Example showed an example wherein induction of cancer cell apoptosis was seen by silencing the RPN2 gene of MCF7-ADR of the breast cancer cells. However, even for other cells where RPN2 genes are highly expressed, for example, cells and tissues of colon cancer, esophagus cancer, ovary cancer, breast cancer or lung cancer, apoptosis is likely to be induced of cancer cells by silencing the RPN2 gene.

Moreover, an example was shown wherein PC-9/CDDP cell of human lung cancer cell, which shows resistance to cisplatin, was used as a cell line which shows resistance to anti-cancer agent. By silencing the RPN2 gene of the PC-9/CDDP cell, induction of cancer cell apoptosis was seen. However, in addition to PC-9/CDDP cell, there has been known a cell line which is resistant to an anti-cancer agent, and of which the parental cell line is a human lung cancer cell line such as PC-14 cell, SBC-3 cell and H69 cell, K562 cell (human leukemia cell line) or p388 cell (mouse lymphocyte-like cell line) and the like. For example, the cell line is PC-14/CDDP, SBC-3/CDDP, SBC-3/ADM, H69/CDDP, K562/ADM, p388/MMC and the like (Herein CDDP refers to cisplatin resistance, ADM refers to adriamycin resistance and MMC refers to mitomycin C resistance). Silencing of RPN2 gene is likely to induce apoptosis as well as in these cells resistant to an anti-cancer agent.

Examples will be shown now wherein RPN2 gene expression is suppressed in human liver cancer or human colon cancer by siRNA.

Test Example 10

HepG2, which is a cell line of human liver cancer, was inoculated into a 96 well plate in 5000/well. The next day, RPN2 siRNA (dsRNA including a sense chain of Sequence No. 3 and an antisense chain of Sequence No. 4) was introduced according to the protocol suggested by Invitrogen Corporation using a gene introduction reagent (Lipofectamine 2000: Invitrogen), to suppress RPN2 gene expression. The control siRNA (dsRNA including a sense chain of Sequence No. 5 and an antisense chain of Sequence No. 6) was introduced as the negative control. At the same time with the siRNA, DOC was added in 1 nM of the final concentration. After the culture for 3 days, in order to determine the cell survival rate in each well, a quantification reagent for the live cells (CellTiter-Glo substrate: Promega KK) was added to each well, and the plate was stirred for 2 minutes, and left for 10 minutes. The luminescence was measured by a luminescence plate reader (ARVO: PerkinElmer).

Figure 13:
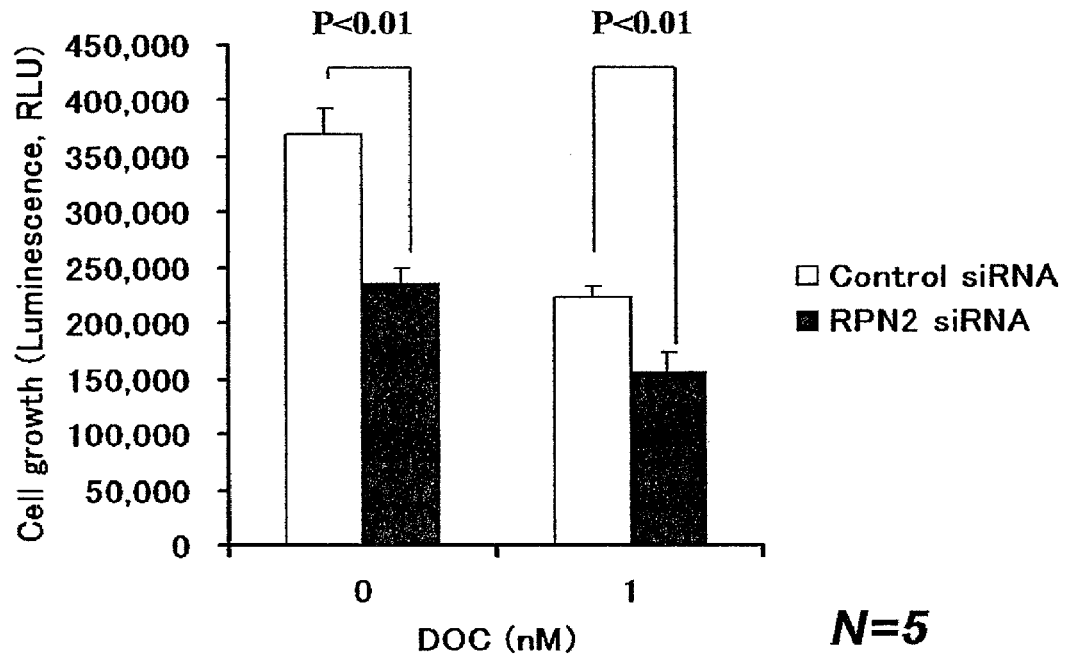
FIG. 13 is a graph showing the result of the RPN2 gene expression suppression test in human liver cancer cells. The test was conducted five times, and the average was taken.

The results are shown in FIG. 13 as the luminescence intensity (RLU) subtracting the luminescence intensity of no cell well. According to FIG. 13, RPN2 siRNA showed cancer cell growth suppression effects alone in HepG2 cell which shows sensitivity to DOC, and also showed actions of potentiating the cancer cell growth suppression effects of DOC.

Test Example 11

HT29, which is a cell line of human colon cancer, was inoculated into a 96 well plate in 500/well. The next day, multiple sequences of RPN2 siRNA were introduced according to the protocol suggested by Dharmacon using a gene introduction reagent (Dharmafect: Dharmacon), to suppress RPN2 gene expression. The control siRNA (dsRNA including a sense chain of Sequence No. 5 and an antisense chain of Sequence No. 6) was introduced as the negative control. After the culture for 3 days, in order to determine the cell survival rate in each well, a quantification reagent (TetraColor ONE: Seikagaku Corporation) for the live cells was added per 10 μl, and cultured further for 2 to 3 hours. The absorbance was measured per each well at 490 nM.

Figure 14:
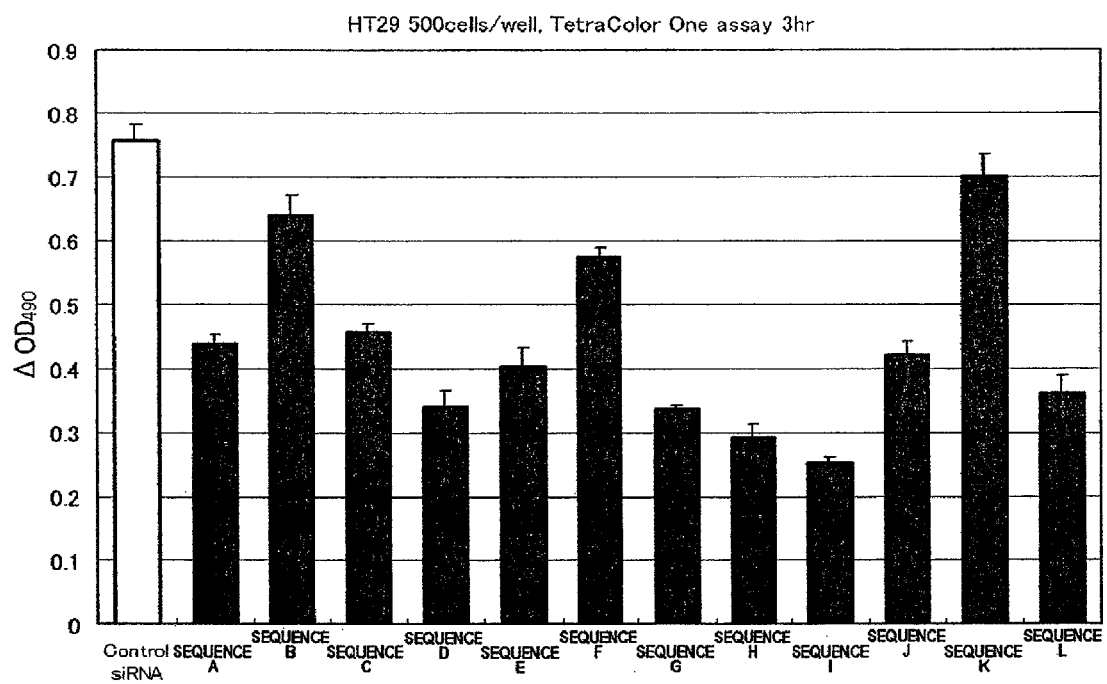
FIG. 14 is a graph showing the results of the RPN2 gene expression suppression test in human colon cancer cells using dsRNAs of various sequences.

The results are shown in FIG. 14 as $\Delta OD_{490}$ subtracting the absorbance of no cell well excluded. The multiple RPN2 siRNAs (Sequences A to L) used in the test have sequences shown below respectively. In addition, Sequences A to L are dsRNAs including the sense chain and the antisense chain shown in Table 2.

Sequence A (dsRNA including a sense chain of Sequence No. 3 and an antisense chain of Sequence No. 4);
Sequence B (dsRNA including a sense chain of Sequence No. 9 and an antisense chain of Sequence No. 10);
Sequence C (dsRNA including a sense chain of Sequence No. 11 and an antisense chain of Sequence No. 12); Sequence D (dsRNA including a sense chain of Sequence No. 13 and an antisense chain of Sequence No. 14);
Sequence E (dsRNA including a sense chain of Sequence No. 15 and an antisense chain of Sequence No. 16);
Sequence F (dsRNA including a sense chain of Sequence No. 17 and an antisense chain of Sequence No. 18);
Sequence G (dsRNA including a sense chain of Sequence No. 19 and an antisense chain of Sequence No. 20);
Sequence H (dsRNA including a sense chain of Sequence No. 21 and an antisense chain of Sequence No. 22);
Sequence I (dsRNA including a sense chain of Sequence No. 23 and an antisense chain of Sequence No. 24);
Sequence J (dsRNA including a sense chain of Sequence No. 25 and an antisense chain of Sequence No. 26);
Sequence K (dsRNA including a sense chain of Sequence No. 27 and an antisense chain of Sequence No. 28);
Sequence L (dsRNA including a sense chain of Sequence No. 29 and an antisense chain of Sequence No. 30)

Any of the sequences showed alone actions of suppressing HT29 cell growth.

TABLE 2

| SEQUENCE NAME | SEQUENCE NO. | Sense | SEQUENCE NO. | Antisense |
| --- | --- | --- | --- | --- |
| Control siRNA | 5 | UAGCGACUAAACACAUCAAUU | 6 | UUGAUGUGUUUAGUCGCUAUU |
| SEQUENCE A | 3 | GGCCACUGUUAAACUAGAACA | 4 | UUCUAGUUUAACAGUGGCCUG |
| SEQUENCE B | 9 | CGUGUACAAGUUUGAACUGdTdT | 10 | CAGUUCAAACUUGUACACGdTdT |
| SEQUENCE C | 11 | GCCAUCCAUUAAGGAGGAUdTdT | 12 | AUCCUCCUUAAUGGAUGGCdTdC |
| SEQUENCE D | 13 | GCAAUGUGGAUUCCCUCUUdTdT | 14 | AAGAGGGAAUCCACAUUGCdTdG |
| SEQUENCE E | 15 | GGUGCCAGAUGCAAAGAAAdTdT | 16 | UUUCUUUGCAUCUGGCACCdTdG |
| SEQUENCE F | 17 | GGAUGUGAGAUCUCUAUUUdTdT | 18 | AAAUAGAGAUCUCACAUCCdTdG |

TABLE 2-continued

TABLE 2

| SEQUENCE NAME | SEQUENCE NO. | Sense | SEQUENCE NO. | Antisense |
|---|---|---|---|---|
| SEQUENCE G | 19 | GGUGCCAGAUGCAAAGAAAdTdT | 20 | UUUCUUUGCAUCUGGCACCdTdG |
| SEQUENCE H | 21 | GGCCACUGUUAAACUAGAAdTdT | 22 | UUCUAGUUUAACAGUGGCCdTdG |
| SEQUENCE I | 23 | GGGUGACAUACCCAGCCAAdTdT | 24 | UUGGCUGGGUAUGUCACCCdGdG |
| SEQUENCE J | 25 | GGGUAACAAUAGGAACAAAdTdT | 26 | UUUGUUCCUAUUGUUACCCdTdC |
| SEQUENCE K | 27 | AAGAUAGCCUGUUCAUGAGUGUCGG | 28 | CCGACACUCAUGAACAGGCUAUCUU |
| SEQUENCE L | 29 | UUAUGGAGUCGGACAAAUGUCUGGU | 30 | ACCAGACAUUUGUCCGACUCCAUAA |

---

The invention claimed is:

1. A method of treating cancer comprising administering to a patient in need thereof a ribophorin II (RPN2) gene expression inhibitor as an anti-cancer agent, wherein the RPN2 gene expression inhibitor is an RPN2-targeted siRNA that suppresses RPN2 gene expression by RNA interference, wherein the cancer being treated is one that is responsive to the RPN2 gene expression inhibitor that is administered, and wherein the administration results in an anti-cancer effect.

2. A method of treating cancer comprising administering to a patient in need thereof an RPN2 gene expression inhibitor as an anti-cancer agent in combination with a drug showing an anti-cancer action, wherein the cancer being treated is one that is responsive to the RPN2 gene expression inhibitor that is administered, and wherein the administration results in an anti-cancer effect.

3. The method of treating cancer as set forth in claim 1, wherein the RPN2 gene expression inhibitor is administered in combination with atelocollagen.

4. The method of treating cancer as set forth in claim 2, wherein the RPN2 gene expression inhibitor is administered in combination with atelocollagen.

5. The method of treating cancer as set forth in claim 2, wherein said drug showing an anti-cancer action is a taxane.

6. The method of treating cancer as set forth in claim 2, wherein said drug showing an anti-cancer action is a platinum-based chemotherapy drug.

7. The method of treating cancer as set forth in claim 1, wherein the cancer is selected from the group consisting of breast cancer, lung cancer, liver cancer, and colon cancer.

8. The method of treating cancer as set forth in claim 1, wherein the cancer is breast cancer.

9. The method of treating cancer as set forth in claim 1, wherein the cancer is lung cancer.

10. The method of treating cancer as set forth in claim 2, wherein the cancer is selected from the group consisting of breast cancer, lung cancer, liver cancer, and colon cancer.

* * * * *

SEQUENCE LISTING

<160> NUMBER OF SEQ ID NOS: 30

<210> SEQ ID NO 1
<211> LENGTH: 2509
<212> TYPE: DNA
<213> ORGANISM: Homo sapiens

<400> SEQUENCE: 1

```
ttccagcgtt gcgagacggt cggttccaag tgggcctggg cgcggggag aggcgggtct      60
gtcctcggga actgcaaggc cctgtgagcg ggaggactgg gatcccggcc gcggctgctg    120
gaagcgtcga agctcagcgg gccgcggaca tgacctgtgc ttagaactca tcctggcccg    180
cagagcctgc cgcgagtccc tggcgtcccc tgtggcgggc tcttggagcc actttcccga    240
gcggaagtca gcccgcggct cggactccgg cgggacctgc tcggaggaat ggcgccgccg    300
ggttcaagca ctgtcttcct gttggccctg acaatcatag ccagcacctg ggctctgacg    360
cccactcact acctcaccaa gcatgacgtg gagagactaa aagcctcgct ggatcgccct    420
ttcacaaatt tggaatctgc cttctactcc atcgtgggac tcagcagcct tggtgctcag    480
gtgccagatg caaagaaagc atgtacctac atcagatcta accttgatcc cagcaatgtg    540
gattccctct tctacgctgc ccaggccagc caggccctct caggatgtga gatctctatt    600
tcaaatgaga ccaaagatct gcttctggca gctgtcagtg aggactcatc tgttacccag    660
atctaccatg cagttgcagc tctaagtggc tttggccttc ccttggcatc ccaagaagca    720
ctcagtgccc ttactgctcg tctcagcaag gaggagactg tgctggcaac agtccaggct    780
ctgcagacag catcccacct gtcccagcag gctgacctga ggagcatcgt ggaggagatt    840
gaggaccttg ttgctcgcct ggatgaactc ggggcgtgt atctccagtt tgaagaagga    900
ctggaaacaa cagcgttatt tgtggctgcc acctacaagc tcatggatca tgtgggact    960
gagccatcca ttaaggagga tcaggtcatc cagctgatga cgcgatctt cagcaagaag   1020
aactttgagt ccctctccga agccttcagc gtggcctctg cagctgctgt gctctcgcat   1080
aatcgctacc acgtgccagt tgtggttgtg cctgagggct ctgcttccga cactcatgaa   1140
caggctatct tgcggttgca agtcaccaat gttctgtctc agcctctgac tcaggccact   1200
gttaaactag aacatgctaa atctgttgct tccagagcca ctgtcctcca gaagacatcc   1260
ttcacccctg tagggatgt ttttgaacta aatttcatga acgtcaaatt ttccagtggt   1320
tattatgact tccttgtcga agttgaaggt gacaaccggt atattgcaaa tacgtagag   1380
```

-continued

```
ctcagagtca agatctccac tgaagttggc atcacaaatg ttgatctttc caccgtggat      1440
aaggatcaga gcattgcacc caaaactacc cgggtgacat acccagccaa agccaagggc      1500
acattcatcg cagacagcca ccagaacttc gccttgttct tccagctggt agatgtgaac      1560
actggtgctg aactcactcc tcaccagaca tttgtccgac tccataacca gaagactggc      1620
caggaagtgg tgtttgttgc cgagccagac aacaagaacg tgtacaagtt tgaactggat      1680
acctctgaaa gaaagattga atttgactct gcctctggca cctacactct ctacttaatc      1740
attggagatg ccactttgaa gaacccaatc ctctggaatg tggctgatgt ggtcatcaag      1800
ttccctgagg aagaagctcc ctcgactgtc ttgtcccaga accttttcac tccaaaacag      1860
gaaattcagc acctgttccg cgagcctgag aagaggcccc ccaccgtggt gtccaataca      1920
ttcactgccc tgatcctctc gccgttgctt ctgctcttcg ctctgtggat ccggattggt      1980
gccaatgtct ccaacttcac ttttgctcct agcacgatta tatttcacct gggacatgct      2040
gctatgctgg gactcatgta tgtctactgg actcagctca acatgttcca gaccttgaag      2100
tacctggcca tcctgggcag tgtgacgttt ctggctggca atcggatgct ggcccagcag      2160
gcagtcaaga gaacagcaca ttagttccag aagaaagatg gaaattctga aaactgaatg      2220
tcaagaaaag gagtcaagaa caattcacag tatgagaaga aaaatggaaa aaaaaaactt      2280
tatttaaaaa agaaaaaagt ccagattgta gttatacttt tgcttgtttt tcagtttccc      2340
caacacacag cagatacctg gtgagctcag atagtctctt tctctgacac tgtgtaagaa      2400
gctgtgaata ttcctaactt acccagatgt tgcttttgaa aagttgaaat gtgtaattgt      2460
tttggaataa agagggtaac aataggaaca aaaaaaaaaa aaaaaaaa               2509
```

<210> SEQ ID NO 2
<211> LENGTH: 23
<212> TYPE: DNA
<213> ORGANISM: Homo sapiens

<400> SEQUENCE: 2
caggccactg ttaaactaga aca                                              23

<210> SEQ ID NO 3
<211> LENGTH: 21
<212> TYPE: RNA
<213> ORGANISM: Homo sapiens

<400> SEQUENCE: 3
ggccacuguu aaacuagaac a                                                21

<210> SEQ ID NO 4
<211> LENGTH: 21
<212> TYPE: RNA
<213> ORGANISM: Homo sapiens

<400> SEQUENCE: 4
uucuaguuua acaguggccu g                                                21

<210> SEQ ID NO 5
<211> LENGTH: 21
<212> TYPE: DNA
<213> ORGANISM: Homo sapiens

<400> SEQUENCE: 5
uagcgacuaa acacaucaau u                                                21

```
<210> SEQ ID NO 6
<211> LENGTH: 21
<212> TYPE: RNA
<213> ORGANISM: Homo sapiens

<400> SEQUENCE: 6
uugauguguu uagucgcuau u                                              21

<210> SEQ ID NO 7
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine

<400> SEQUENCE: 7
cuuacgcuga guacuucgan n                                              21

<210> SEQ ID NO 8
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine

<400> SEQUENCE: 8
ucgaaguacu cagcguaagn n                                              21

<210> SEQ ID NO 9
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine

<400> SEQUENCE: 9
cguguacaag uuugaacugn n                                              21

<210> SEQ ID NO 10
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine

<400> SEQUENCE: 10
caguucaaac uuguacacgn n                                              21
```

```
<210> SEQ ID NO 11
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine

<400> SEQUENCE: 11
gccauccauu aaggaggaun n                                            21

<210> SEQ ID NO 12
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(20)
<223> OTHER INFORMATION: Deoxythymidine
<220> FEATURE:
<221> NAME/KEY: modified_base
<222> LOCATION: (21)..(21)
<223> OTHER INFORMATION: Deoxycytidine

<400> SEQUENCE: 12
auccuccuua auggauggcn n                                            21

<210> SEQ ID NO 13
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine

<400> SEQUENCE: 13
gcaaugugga uucccucuun n                                            21

<210> SEQ ID NO 14
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(20)
<223> OTHER INFORMATION: Deoxythymidine
<220> FEATURE:
<221> NAME/KEY: modified_base
<222> LOCATION: (21)..(21)
<223> OTHER INFORMATION: Deoxyguanosine

<400> SEQUENCE: 14
aagagggaau ccacauugcn n                                            21

<210> SEQ ID NO 15
<211> LENGTH: 21
<212> TYPE: DNA
<213> ORGANISM: Homo sapiens
```

-continued

```
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine

<400> SEQUENCE: 15
ggugccagau gcaaagaaan n                                               21

<210> SEQ ID NO 16
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(20)
<223> OTHER INFORMATION: Deoxythymidine
<220> FEATURE:
<221> NAME/KEY: modified_base
<222> LOCATION: (21)..(21)
<223> OTHER INFORMATION: Deoxyguanosine

<400> SEQUENCE: 16
uuucuuugca ucuggcaccn n                                               21

<210> SEQ ID NO 17
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine

<400> SEQUENCE: 17
ggaugugaga ucucuauuun n                                               21

<210> SEQ ID NO 18
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(20)
<223> OTHER INFORMATION: Deoxythymidine
<220> FEATURE:
<221> NAME/KEY: modified_base
<222> LOCATION: (21)..(21)
<223> OTHER INFORMATION: Deoxyguanosine

<400> SEQUENCE: 18
aaauagagau cucacauccn n                                               21

<210> SEQ ID NO 19
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
```

```
<220> FEATURE:
<221> NAME/KEY: modified_base
<222> LOCATION: (20)..(21)
<223> OTHER INFORMATION: Deoxythymidine

<400> SEQUENCE: 19
ggugccagau gcaaagaaan n                                                    21

<210> SEQ ID NO 20
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(20)
<223> OTHER INFORMATION: Deoxythymidine
<220> FEATURE:
<221> NAME/KEY: modified_base
<222> LOCATION: (21)..(21)
<223> OTHER INFORMATION: Deoxyguanosine

<400> SEQUENCE: 20
uuucuuugca ucuggcaccn n                                                    21

<210> SEQ ID NO 21
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine

<400> SEQUENCE: 21
ggccacuguu aaacuagaan n                                                    21

<210> SEQ ID NO 22
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(20)
<223> OTHER INFORMATION: Deoxythymidine
<220> FEATURE:
<221> NAME/KEY: modified_base
<222> LOCATION: (21)..(21)
<223> OTHER INFORMATION: Deoxyguanosine

<400> SEQUENCE: 22
uucuaguuua acaguggccn n                                                    21

<210> SEQ ID NO 23
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine
```

-continued

```
<400> SEQUENCE: 23
gggugacaua cccagccaan n                                              21

<210> SEQ ID NO 24
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxyguanosine

<400> SEQUENCE: 24
uuggcugggu augucacccn n                                              21

<210> SEQ ID NO 25
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(21)
<223> OTHER INFORMATION: Deoxythymidine

<400> SEQUENCE: 25
ggguaacaau aggaacaaan n                                              21

<210> SEQ ID NO 26
<211> LENGTH: 21
<212> TYPE: DNA
<213> ORGANISM: Homo sapiens
<220> FEATURE:
<223> OTHER INFORMATION: Description of Combined DNA/RNA Molecule: siRNA
      oligonucleotide
<220> FEATURE:
<221> NAME/KEY: modified_base
<222> LOCATION: (20)..(20)
<223> OTHER INFORMATION: Deoxythymidine
<220> FEATURE:
<221> NAME/KEY: modified_base
<222> LOCATION: (21)..(21)
<223> OTHER INFORMATION: Deoxycytidine

<400> SEQUENCE: 26
uuuguuccua uuguuacccn n                                              21

<210> SEQ ID NO 27
<211> LENGTH: 25
<212> TYPE: RNA
<213> ORGANISM: Homo sapiens

<400> SEQUENCE: 27
aagauagccu guucaugagu gucgg                                          25

<210> SEQ ID NO 28
<211> LENGTH: 25
<212> TYPE: RNA
<213> ORGANISM: Homo sapiens

<400> SEQUENCE: 28
ccgacacuca ugaacaggcu aucuu                                          25
```

```
<210> SEQ ID NO 29
<211> LENGTH: 25
<212> TYPE: RNA
<213> ORGANISM: Homo sapiens

<400> SEQUENCE: 29
uuauggaguc ggacaaaugu cuggu                                           25

<210> SEQ ID NO 30
<211> LENGTH: 25
<212> TYPE: RNA
<213> ORGANISM: Homo sapiens

<400> SEQUENCE: 30
accagacauu uguccgacuc cauaa                                           25
```